(12) United States Patent
Akbarian et al.

(10) Patent No.: US 10,959,785 B2
(45) Date of Patent: Mar. 30, 2021

(54) TISSUE SHAVING INSTRUMENT WITH NAVIGATION SENSOR

(71) Applicant: Acclarent, Inc., Irvine, CA (US)

(72) Inventors: Fatemeh Akbarian, Rancho Palos Verdes, CA (US); Itzhak Fang, Irvine, CA (US); Azhang Hamlekhan, Irvine, CA (US); Jetmir Palushi, Irvine, CA (US); Ehsan Shameli, Irvine, CA (US); David A. Smith, Jr., Lake Forest, CA (US)

(73) Assignee: Acclarent, Inc., Irvine, CA (US)

( * ) Notice: Subject to any disclaimer, the term of this patent is extended or adjusted under 35 U.S.C. 154(b) by 352 days.

(21) Appl. No.: 15/839,274

(22) Filed: Dec. 12, 2017

(65) Prior Publication Data
US 2019/0175282 A1    Jun. 13, 2019

(51) Int. Cl.
| | |
|---|---|
| *A61B 34/20* | (2016.01) |
| *A61B 17/32* | (2006.01) |
| *A61B 1/233* | (2006.01) |
| *A61B 17/24* | (2006.01) |
| *A61B 17/34* | (2006.01) |

(Continued)

(52) U.S. Cl.
CPC .............. *A61B 34/20* (2016.02); *A61B 1/233* (2013.01); *A61B 17/24* (2013.01); *A61B 17/32002* (2013.01); *A61B 10/0283* (2013.01); *A61B 17/3417* (2013.01); *A61B 34/70* (2016.02); *A61B 90/10* (2016.02); *A61B 2034/2051* (2016.02); *A61B 2034/2072* (2016.02); *A61B 2217/005* (2013.01)

(58) Field of Classification Search
CPC .... A61B 17/32002; A61B 34/20; A61B 1/233
See application file for complete search history.

(56) References Cited

U.S. PATENT DOCUMENTS

| | | |
|---|---|---|
| 7,720,521 B2 | 5/2010 | Chang et al. |
| 8,123,722 B2 | 2/2012 | Chang et al. |

(Continued)

FOREIGN PATENT DOCUMENTS

WO     WO 2017/052704 A2    3/2017

OTHER PUBLICATIONS

International Search Report and Written Opinion dated Mar. 19, 2019 for International Application No. PCT/IB2018/059871, 12 pages.

(Continued)

*Primary Examiner* — Sarah A Simpson
(74) *Attorney, Agent, or Firm* — Frost Brown Todd LLC

(57) ABSTRACT

A surgical instrument and method of tracking the surgical instrument includes a shaft, a cutting member, and navigation system. The shaft has a shaft lumen, a shaft window, and a shaft edge. The cutting member is disposed within the shaft lumen and is configured to cyclically move from a first position to a second position relative to the shaft. The cutting member includes a cutting window opening, a cutting edge, and a suction lumen to cut the tissue portion with the cutting member in the first position. The navigation system includes a navigation sensor positioned on at least one of the shaft or the cutting member that is configured to be tracked within a patient for identifying a positional movement of the shaft or the cutting member within the patient.

16 Claims, 13 Drawing Sheets

(51) Int. Cl.
  *A61B 34/00* (2016.01)
  *A61B 10/02* (2006.01)
  *A61B 90/10* (2016.01)

(56) References Cited

U.S. PATENT DOCUMENTS

| | | | |
|---|---|---|---|
| 8,190,389 | B2 | 5/2012 | Kim et al. |
| 8,320,711 | B2 | 11/2012 | Altmann et al. |
| 8,702,626 | B1 | 4/2014 | Kim et al. |
| 9,167,961 | B2 | 10/2015 | Makower et al. |
| 9,198,736 | B2 | 12/2015 | Kim et al. |
| 9,211,163 | B1 | 12/2015 | Jaramaz et al. |
| 2002/0165448 | A1 | 11/2002 | Ben-Haim et al. |
| 2004/0220461 | A1* | 11/2004 | Schwartz ............. A61B 5/0422 600/374 |
| 2006/0004286 | A1* | 1/2006 | Chang ................... A61B 34/20 600/435 |
| 2006/0004323 | A1 | 1/2006 | Chang et al. |
| 2006/0142656 | A1 | 6/2006 | Malackowski et al. |
| 2007/0208252 | A1 | 9/2007 | Makower |
| 2008/0091193 | A1* | 4/2008 | Kauphusman ..... A61B 18/1492 606/41 |
| 2011/0060214 | A1 | 3/2011 | Makower |
| 2012/0172716 | A1* | 7/2012 | Sela ....................... A61B 5/062 600/424 |
| 2014/0148729 | A1 | 5/2014 | Schmitz et al. |
| 2014/0200444 | A1 | 7/2014 | Kim et al. |
| 2014/0206985 | A1 | 7/2014 | Kariv |
| 2014/0364725 | A1 | 12/2014 | Makower |
| 2016/0008083 | A1 | 1/2016 | Kesten et al. |
| 2016/0310042 | A1 | 10/2016 | Kesten et al. |
| 2016/0346036 | A1* | 12/2016 | Orczy-Timko ........ A61B 17/32 |
| 2017/0056055 | A1* | 3/2017 | Truckai .......... A61B 17/320068 |
| 2019/0015127 | A1* | 1/2019 | Cheng ................... A61B 34/20 |

OTHER PUBLICATIONS

U.S. Appl. No. 15/795,473, filed Oct. 27, 2017, entitled, "Tissue Shaving Instrument."

U.S. Appl. No. 62/555,824, filed Sep. 8, 2017, entitled, "Apparatus to Secure Field Generating Device to Chair."

* cited by examiner

TISSUE SHAVING INSTRUMENT WITH NAVIGATION SENSOR

BACKGROUND

Surgical cutting instruments configured for removal of lesions, polyps and fibroids within the nasal cavity are known. Some configurations may include an elongated inner member rotatably coaxially disposed within a tubular outer member. The distal end of the outer member includes an opening, and the distal end of the inner member includes cutting edges. The proximal ends of the two members may be connected to a handle directly or via a detachable hub. The inner member may be hollow and in communication with an aspiration port so that severed tissue, etc. can be aspirated out through the hollow member. The cutting edges can have any various configurations suitable for the particular type of tissue or bone cutting to be done, with the opening configured to cooperate with the specific cutting edge configuration.

To use such surgical cutting instrument to address tissue or bone, the opening/cutting edge is advanced to the target surgical site, and the opening positioned adjacent the tissue or bone to be removed. The opening may be repositioned to address tissue which could not be accessed with the instrument in the previous position. Surgical cutting instruments with a fixed opening allow surgeons to cut only in the direction of the fixed opening cutting. To access, cut and remove tissue at various locations, surgeons have to reposition the instrument at various angles; or in some instances, change to other instruments having a more appropriately arranged opening.

It may be desirable to access, cut and remove tissue and bone at various locations without having to reposition or change the surgical instrument. While several different surgical instruments and methods of use have been made for tissue and bone removal within the nasal cavity, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
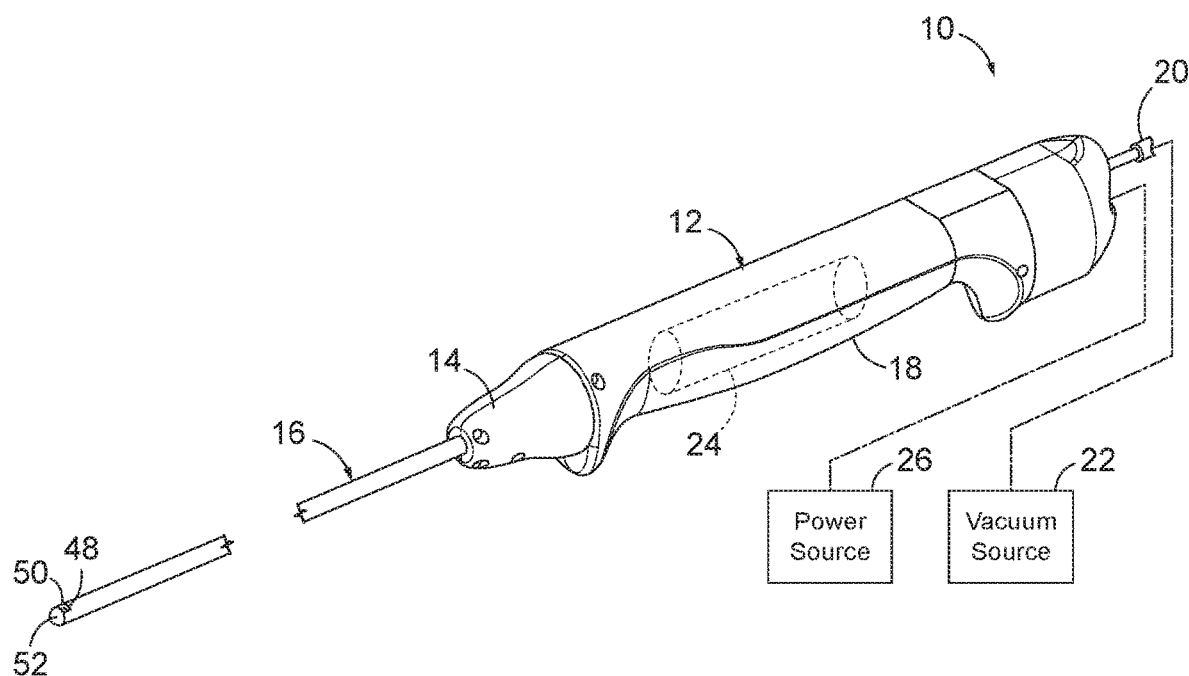
FIG. 1 depicts a perspective view of an exemplary surgical cutting instrument having a handle assembly and a first shaft assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "front," "side," "axial," "longitudinal," "lateral," and "transverse," also are used herein for reference to relative positions and directions. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Surgical Cutting Instrument

Figure 2:
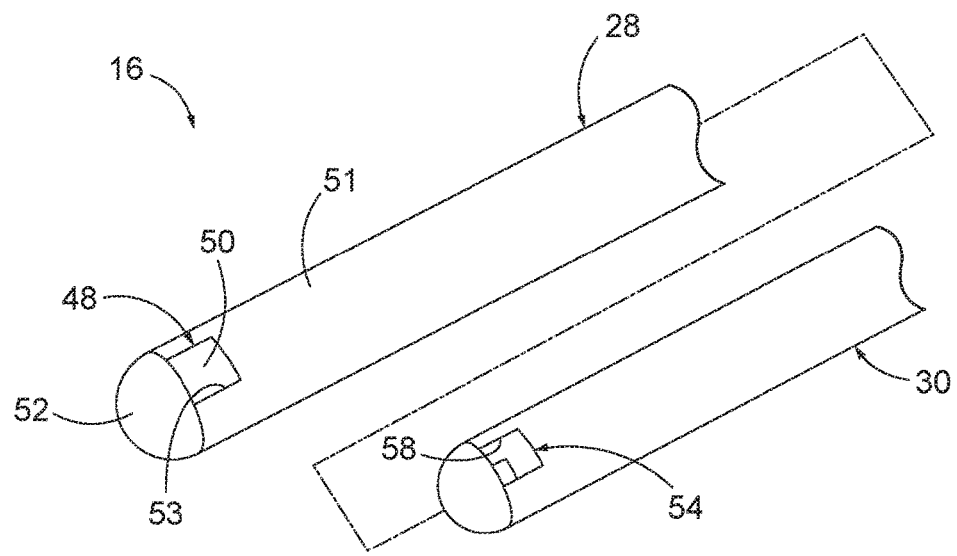
FIG. 2 depicts an exploded perspective fragmentary view of the shaft assembly of FIG. 1 having a shaft and a cutting member.

FIG. 1-2 show an exemplary surgical cutting instrument (10) that may be used to remove tissue and bone from the nasal cavity, as well as from any other suitable location. Surgical cutting instrument (10) of the present example includes a handle assembly (12), a hub (14), and a first shaft assembly (16) extending distally from handle assembly (12). Handle assembly (12) has a handle (18) which may be of any suitable configuration. Handle (18) may include controls for the operation of surgical cutting instrument (10), or the controls may be located remotely. Surgical cutting instrument (10) further includes a suction port (20) operatively connected to a vacuum source (22) and configured to enable aspiration of tissue, such as a bone tissue, from a surgical site. Rotational motion is delivered by a motorized drive assembly (24) within handle assembly (12) to shaft assembly (16) in the present example, although any suitable rotational or oscillatory motion source may be utilized. For example, such motion source may be housed within handle assembly (12) or may be external and connectable to handle assembly (12). A power source (26) connects to motorized drive assembly (24) to power surgical cutting instrument (10) for use. In addition or alternatively, handle assembly (12) may house a battery (not shown).

Shaft assembly (16) generally includes an outer shaft (28) and an inner cutting member (30) collectively configured to receive and remove tissue from the surgical site. Cutting member (30), which is illustrated as a tube, is disposed within a longitudinally extending lumen (32) of shaft (28). Cutting member (30) is configured to be rotated about a longitudinal axis (42) of shaft assembly (16) at a distal portion. Although shaft assembly (16) is depicted as rigid, all or a portion of shaft assembly (16) may be flexible, with longitudinal axis (42) comprising a series of cross-sectional centers. Cutting member (30) defines a lumen and extends proximally to handle assembly (12) and connects to motorized drive assembly (24), which rotatably drives cutting member (30) relative to shaft (28). In the present example, shaft (28) is formed of polycarbonate and cutting member (30) is formed of stainless steel. Of course, shaft (28) and cutting member (30) may be formed of one or more alternative materials in accordance with the invention described herein. The invention is thus not intended to be unnecessarily limited to manufacture with polycarbonate and stainless steel. While the present example of cutting member (30) is a hollow tube, cutting member (30) is not limited to being tubular and defining its own lumen (32).

Shaft (28) includes a window region (48) having a shaft window opening (50) at distal portion. Distal portion includes a tubular sidewall (51) that distally terminates in a curved end, such as a generally hemispherical end (52). Shaft window opening (50) extends through tubular sidewall (51) of shaft (28) into central lumen (40) and is in fluid communication with the environment surrounding shaft (28). Shaft window opening (50) faces radially outward relative to longitudinal axis (42) such that tissue is configured to be radially received through shaft window opening (50) into central lumen (40) in a radially inward direction. Shaft window opening (50) is surrounded by a relatively dull edge (53).

Cutting member (30) includes a cutting window opening (54) at distal portion of cutting member (30). Cutting window opening (54) is configured to longitudinally align with shaft window opening (50) and includes a cutting edge (58) extending therealong. It is noted that less than the entirety of cutting edge (58) may be configured for cutting tissue against an opposing edge (53) of shaft (28). At least a portion of cutting edge (58) is disposed to move adjacent to and across at least a portion of window region (48) when cutting member (30) is rotated or oscillated about longitudinal axis (42). By way of example, as cutting member (30) moves in a clockwise direction, edge (53) of window region (48) provides an opposing surface to cutting edge (58) whereby tissue may be severed to remove a cut tissue portion therefrom. Cutting edge (58) and edge (53) may have any configuration which suitably cooperates with the other to sever tissue, such as a knife edge, a serrated edge, bipolar, monopolar or harmonic energy modality, or laser activated cutting edge.

The extent of movement and position of cutting edge (58) relative to edge (53) is sufficient to separate tissue, whether by severing, tearing or any other mechanism. For example, cutting edge (58) may cyclically move across at least a portion of window region (48). Further clockwise movement of cutting member (30) will advance cutting edge (58) past edge (53), such as results from oscillation about longitudinal axis (42) or from full rotation about longitudinal axis (42).

With continued reference to FIGS. 1-2, vacuum source (22) generates suction in a proximal direction along longitudinal axis (42) toward suction port (20). Without tissue blocking cutting window opening (54), such suction proximally withdraws a window airflow therethrough along lumen. However, once tissue is respectively introduced into window opening (54), suction effectively draws tissue into window opening (54) for resection while tissue blocks airflow along lumen. Airflow through lumen essentially terminates such that vacuum source (22) accumulates the vacuum within lumen. Such termination of airflow may generally be referred to as a stalled airflow within lumen. Additional details regarding airflow through lumen and aspiration vents for improving such airflow are discussed in alternative examples described in U.S. patent application Ser. No. 15/795,473, entitled "Tissue Shaving Instrument," filed Oct. 27, 2017, issued as U.S. Pat. No. 10,631,890 on Apr. 28, 2020, the disclosure of which is incorporated by reference herein.

II. Image Guided Surgery Navigation System

Figure 3:
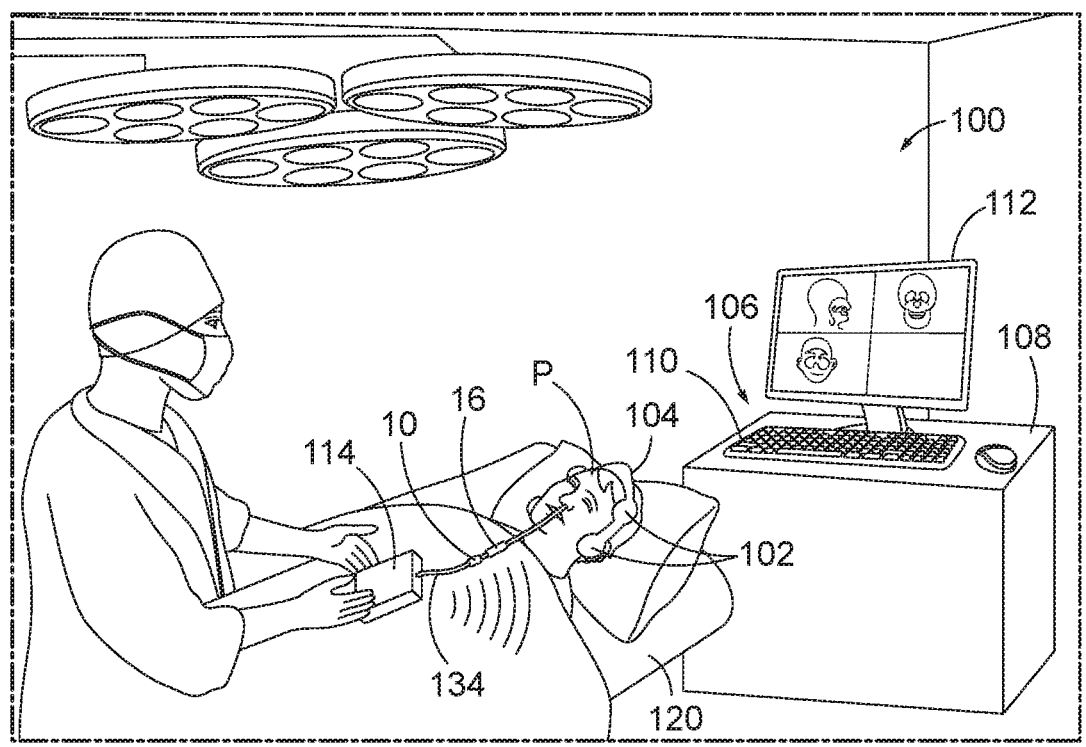
FIG. 3 depicts a schematic view of an exemplary image guided surgery (IGS) navigation system for use with the surgical cutting instrument assembly of FIG. 1.

FIG. 3 shows an exemplary image-guided surgery (IGS) navigation system (100) configured to perform a tissue removal procedure within a sinus passage a patient (P). As described in greater detail below, IGS navigation system (100) includes a computer used to obtain a real-time correlation of the location of an instrument that has been inserted into the patient's body, such as shaft assembly (16) of surgical cutting instrument (10), to a set of preoperatively obtained images (e.g., a CT or MRI scan, 3-D map, etc.) so as to superimpose the current location of the instrument on the preoperatively obtained images. In some instances, a digital tomographic scan (e.g., CT or MRI, 3-D map, etc.) of the operative field is obtained prior to surgery. A specially programmed computer is then used to convert the digital tomographic scan data into a digital map. During surgery, an instrument having one or more sensors (e.g., electromagnetic coils that emit electromagnetic fields and/or are responsive to externally generated electromagnetic fields) mounted thereon is used to perform the procedure while the sensors send data to the computer, indicating the current position of the surgical instrument. The computer correlates the data it receives from the instrument-mounted sensors with the digital map that was created from the preoperative tomographic scan. The tomographic scan images are displayed on a video monitor along with an indicator (e.g., cross hairs or an illuminated dot, etc.) showing the real-time position of the surgical instrument relative to the anatomical structures shown in the scan images. In this manner, the surgeon is able to know the precise position of the sensor-equipped instrument by viewing the video monitor, even if the surgeon is unable to directly visualize the instrument itself at its current location within the body.

IGS navigation system (100) incorporates shaft assembly (16) described above, and may further incorporate other suitable shaft assemblies (216, 316, 516) discussed below in greater detail. Generally, IGS navigation system (100) is configured to implement a navigation sensor (not shown) of shaft assembly (16) to provide real-time location tracking of distal end of shaft assembly (16) within the patient (P) during a surgical procedure, and thereby facilitate accurate positioning of shaft assembly (16) within the patient (P). While the present example of shaft assembly (16) does not illustrate such navigation sensors, various examples of navigations sensors (266, 366a, 366b, 366c, 466, 466', 466", 566) are discussed below in greater detail. Navigation system (100) is described in connection with the positioning of shaft assembly (16) and variations thereof within the sinus passage, but it will be appreciated that IGS navigation system (100) may also be employed in procedures for accessing and treating various other anatomical passageways of a patient with shaft assembly (16) and the variations thereof described below.

Figure 4:
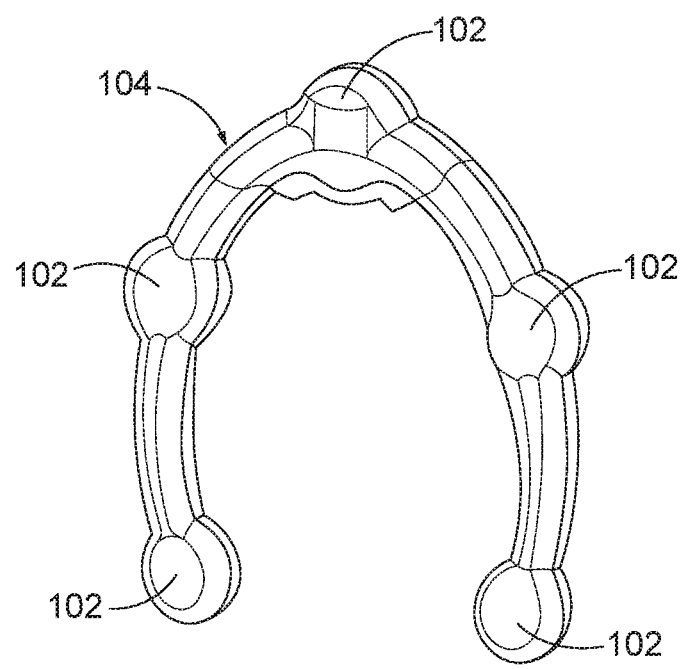
FIG. 4 depicts a perspective view of a frame component of the image-guided surgery navigation system of FIG. 3.

IGS navigation system (100) of the present example includes a set of magnetic field generators (102). Before a surgical procedure begins, field generators (102) are positioned about the head of the patient (P). As best shown in FIG. 4, in the present example field generators (102) arranged integrally within a frame (104) having a horseshoe-like shape and configured to be positioned about the patient's head. In the example of FIG. 3, patient (P) is positioned on a medical procedure table (120), and frame (104) is positioned above table (120) and about the patient's head. Frame (104) may be mounted to any suitable support structure (not shown), which may be coupled directly to medical procedure table (120) or provided independently from table (120), such as a floor-mounted stand. In other examples, frame (104) may be secured directly to the head of patient (P). It should be understood that field generators (102) may be positioned at various other suitable locations relative to patient (P), and on various other suitable structures.

Figure 6:
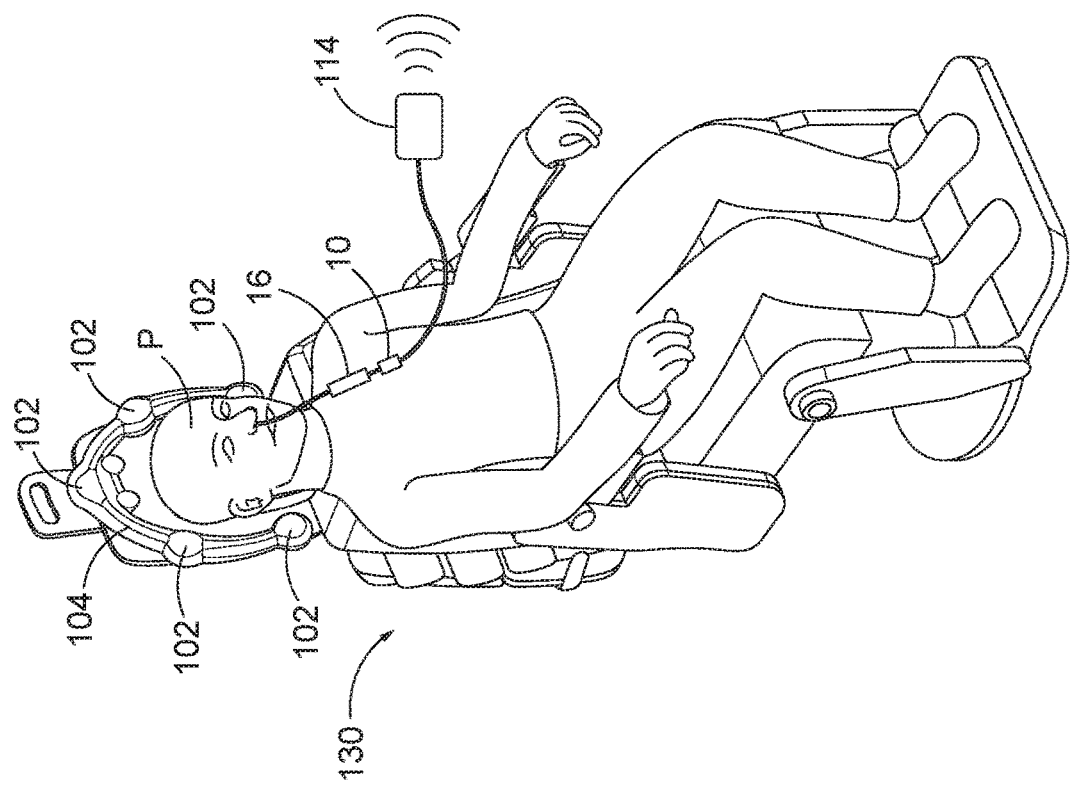
FIG. 6 depicts a perspective view of a patient seated in the medical procedure chair of FIG. 5, with the image-guided surgery navigation system of FIG. 3 being used to perform a procedure on the patient while seated in the chair.
Figure 5:
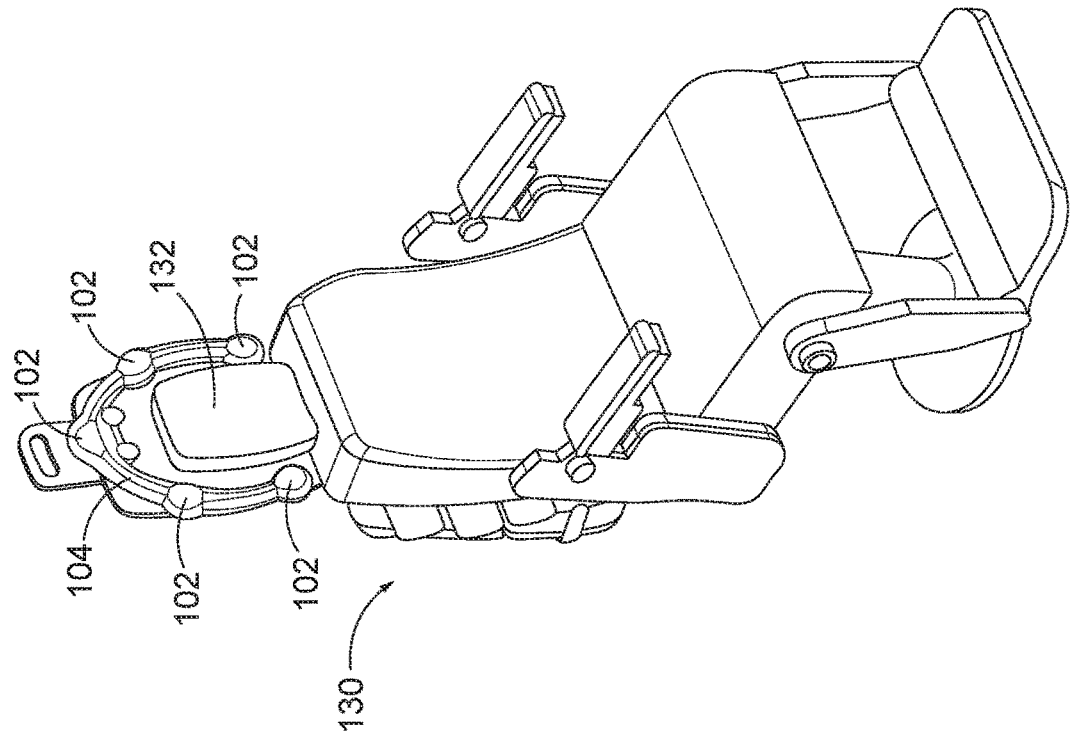
FIG. 5 depicts a perspective view of an exemplary medical procedure chair, with the frame component of the image-guided surgery navigation system of FIG. 4 mounted to the chair.

FIGS. 5 and 6 show another exemplary implementation of IGS navigation system (100), in which patient (P) is seated in a medical procedure chair (130). Frame (104) is mounted to a headrest (132) of chair (130) such that frame (104) extends about the head of patient (P) when seated in chair (130). Medical procedure chair (130) may be configured according to one or more teachings of U.S. Patent App. No. 62/555,824, entitled "Apparatus to Secure Field Generating Device to Chair," filed Sep. 8, 2017, the disclosure of which is incorporated by reference herein.

Field generators (102) of IGS navigation system (100) are operable to transmit alternating magnetic fields of different frequencies into a region in proximity to frame (104), and thereby generate an electromagnetic field in the region. In the present example, field generators (102) and frame (104) are arranged relative to the patient (P) such that the resulting electromagnetic field is formed about the patient's head. In other examples, field generators (102) and frame (104) may be suitably arranged in various other manners so as to generate an electromagnetic field about various other portions of the patient's body. Various suitable components that may be used to form and drive field generators (102) will be apparent to those of ordinary skill in the art in view of the teachings herein.

Field generators (102) enable tracking of the position of navigation sensor (not shown), and thus, distal end of shaft assembly (16) with navigation sensor (not shown) therein, is tracked while moving through the electromagnetic field generated by field generators (102). In particular, as described in greater detail below, electromagnetic navigation sensor (not shown) of shaft assembly (16) is configured to interact with the electromagnetic field and generate an electric signal in response to movement of sensor (not shown) through the electromagnetic field. Navigation sensor (not shown) then communicates this signal to a processor (106) of IGS navigation system (100). Processor (106), in turn, receives the signal and determines the three-dimensional location of navigation sensor (not shown), and a distal end portion of shaft assembly (16) at which sensor (not shown) is arranged, within the electromagnetic field and thus the patient.

Processor (106) of IGS navigation system (100) comprises a processing unit that communicates with one or more memories, and is configured to control field generators (102) and other elements of IGS navigation system (100). In the present example, processor (106) is mounted in a console (108), which comprises operating controls (110) that include a keypad and/or a pointing device such as a mouse or trackball. A physician uses operating controls (110) to interact with processor (106) while performing the surgical procedure. Processor (106) uses software stored in a memory of processor (106) to calibrate and operate system (100). Such operation includes driving field generators (102), processing data received from navigation sensor (not shown), processing data from operating controls (110), and driving display screen (112). The software may be downloaded to processor (106) in electronic form, over a network, for example, or it may, alternatively or additionally, be provided and/or stored on non-transitory tangible media, such as magnetic, optical, or electronic memory.

Processor (106) is further operable to provide video in real time via display screen (112), showing the position of distal end of shaft assembly (16) in relation to a video camera image of the patient's head, a CT scan image of the patient's head, and/or a computer generated three-dimensional model of the anatomy within and adjacent to the patient's nasal cavity. Display screen (112) may display such images simultaneously and/or superimposed on each other. Moreover, display screen (112) may display such images during the surgical procedure. Such displayed images may also include graphical representations of instruments that are inserted in the patient's head, such as shaft assembly (16), such that the physician may view the virtual rendering of the instrument at its actual location in real time. Such graphical representations may look like the instrument or may be a much simpler representation such as a dot, crosshairs, etc. By way of example only, display screen (112) may provide images in accordance with at least some of the teachings of U.S. Pat. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the physician is simultaneously using an endoscope, the endoscopic image may also be provided on display screen (112). The images provided through display screen (112) may assist the physician in maneuvering and otherwise manipulating instruments within the patient's head.

Any suitable device may be used to generate a three-dimensional model of the internal anatomy of the portion of the patient's body (e.g., head) about which the electromagnetic field is generated and into which shaft assembly (16) is to be inserted for conducting a treatment procedure. By way of example only, such a model may be generated in accordance with at least some of the teachings of U.S. Pat. Pub. No. 2016/0310042, entitled "System and Method to Map Structures of Nasal Cavity," published Oct. 27, 2016, issued as U.S. Pat. No. 10,362,965 on Jul. 30, 2019, the disclosure of which is incorporated by reference herein. Still other suitable ways in which a three-dimensional anatomical model may be generated will be apparent to those of ordinary skill in the art in view of the teachings herein. It should also be understood that, regardless of how or where the three-dimensional model is generated, the model may be stored on console (108). Console (108) may thus render images of at least a portion of the model via display screen (112), and further render real-time video images of the position of distal end of shaft assembly (16) in relation to the model via display screen (112).

In addition to connecting with processor (106) and operating controls (110), console (108) may also connect with other elements of IGS navigation system (100). For instance, as shown in FIG. 3, a communication unit (114) may be coupled with shaft assembly (16) via a wire (134). Communication unit (114) of this example is configured to provide wireless communication of data and other signals between console (108) and navigation sensor (not shown) of shaft assembly (16). In some versions, communication unit (114) simply communicates data or other signals from navigation sensor (not shown) to console (108) uni-directionally, without also communicating data or other signals from console (108). In some other versions, communication unit (114) provides bi-directional communication of data or other signals between navigation sensor (not shown) and console (108). While communication unit (114) of the present example couples with console (108) wirelessly, some other versions may provide wired coupling between communication unit (114) and console (108). Various other suitable features and functionality that may be incorporated into communication unit (114) will be apparent to those of ordinary skill in the art in view of the teachings herein.

In addition to, or in lieu of, having the components and operability described herein, IGS navigation system (100) may be constructed and operable in accordance with at least some of the teachings of U.S. Pat. No. 8,702,626, entitled "Guidewires for Performing Image Guided Procedures," issued Apr. 22, 2014, the disclosure of which is incorporated by reference herein; U.S. Pat. No. 8,320,711, entitled "Anatomical Modeling from a 3-D Image and a Surface Mapping," issued Nov. 27, 2012, the disclosure of which is incorporated by reference herein; U.S. Pat. No. 8,190,389, entitled "Adapter for Attaching Electromagnetic Image Guidance Components to a Medical Device," issued May 29, 2012, the disclosure of which is incorporated by reference herein; U.S. Pat. No. 8,123,722, entitled "Devices, Systems and Methods for Treating Disorders of the Ear, Nose and Throat," issued Feb. 28, 2012, the disclosure of which is incorporated by reference herein; and U.S. Pat. No. 7,720,521, entitled "Methods and Devices for Performing Procedures within the Ear, Nose, Throat and Paranasal Sinuses," issued May 18, 2010, the disclosure of which is incorporated by reference herein.

Similarly, in addition to, or in lieu of, having the components and operability described herein, IGS navigation system (100) may be constructed and operable in accordance with at least some of the teachings of U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein; U.S. Pat. Pub. No. 2014/0200444, entitled "Guidewires for Performing Image Guided Procedures," published Jul. 17, 2014, now abandoned, the disclosure of which is incorporated by reference herein; U.S. Pat. No. 9,198,736, entitled "Adapter for Attaching Electromagnetic Image Guidance Components to a Medical Device," issued Dec. 1, 2015, the disclosure of which is incorporated by reference herein; U.S. Pat. Pub. No. 2011/0060214, entitled "Systems and Methods for Performing Image Guided Procedures within the Ear, Nose, Throat and Paranasal Sinuses," published Mar. 10, 2011, now abandoned, the disclosure of which is incorporated by reference herein; U.S. Pat. No. 9,167,961, entitled "Methods and Apparatus for Treating Disorders of the Ear Nose and Throat," issued Oct. 27, 2015, the disclosure of which is incorporated by reference herein; and U.S. Pat. Pub. No. 2007/0208252, entitled "Systems and Methods for Performing Image Guided Procedures within the Ear, Nose, Throat and Paranasal Sinuses," published Sep. 6, 2007, now abandoned, the disclosure of which is incorporated by reference herein.

III. Shaft Assembly and Navigation Sensor Arrangements for a Surgical Cutting Instrument As discussed above in greater detail, shaft assembly (16) may be tracked within the patient, such as by IGS navigation system (100). Shaft assembly (16) may be fitted with a navigation sensor (266, 366a, 366b, 366c, 466, 466', 466", 566) that communicates with IGS navigation system (100) or other like navigation system configured to track a positional movement of navigation sensor (266, 366a, 366b, 366c, 466, 466', 466", 566). By tracking the positional movement of navigation sensor (266, 366a, 366b, 366c, 466, 466', 466", 566), IGS navigation system (100) in turn calculates the positional movement of one or more portions of shaft assembly (16), such as distal end (52) or shaft window opening (50). While IGS navigation system (100) incorporates field generators (102) for such tracking, other exemplary navigation systems may track positional movement of navigation sensor (266, 366a, 366b, 366c, 466, 466', 466", 566) according to an alternative mechanism and method. The invention is thus not intended to be unnecessarily limited to use with IGS navigation system (100).

Various shaft assemblies (216, 316, 516) are described below that incorporate one or more of such navigation sensors (266, 366a, 366b, 366c, 466, 466', 466", 566) for tracking the positional movement of shaft assemblies (216, 316, 516) in use. One or more features of shaft assemblies (216, 316, 516) may be incorporated into shaft assembly (16) discussed above. Indeed, any one of navigation sensors (266, 366a, 366b, 366c, 466, 466', 466", 566) may be replaced by another of navigation sensors (266, 366a, 366b, 366c, 466, 466', 466", 566) or combined therewith to achieve the desired tracking of the positional movement of shaft assemblies (16, 216, 316, 516). To this end, like numbers provided below indicate like features discussed above in greater detail. As used herein, the term "positional movement" generally refers to any tracked component of shaft assemblies (16, 216, 316, 516) position and/or movement thereto. Such "positional movement" may thus include, but is not limited to, a tracked position, orientation, speed, velocity, or acceleration.

A. Integrated Navigation Sensor

Figure 7:
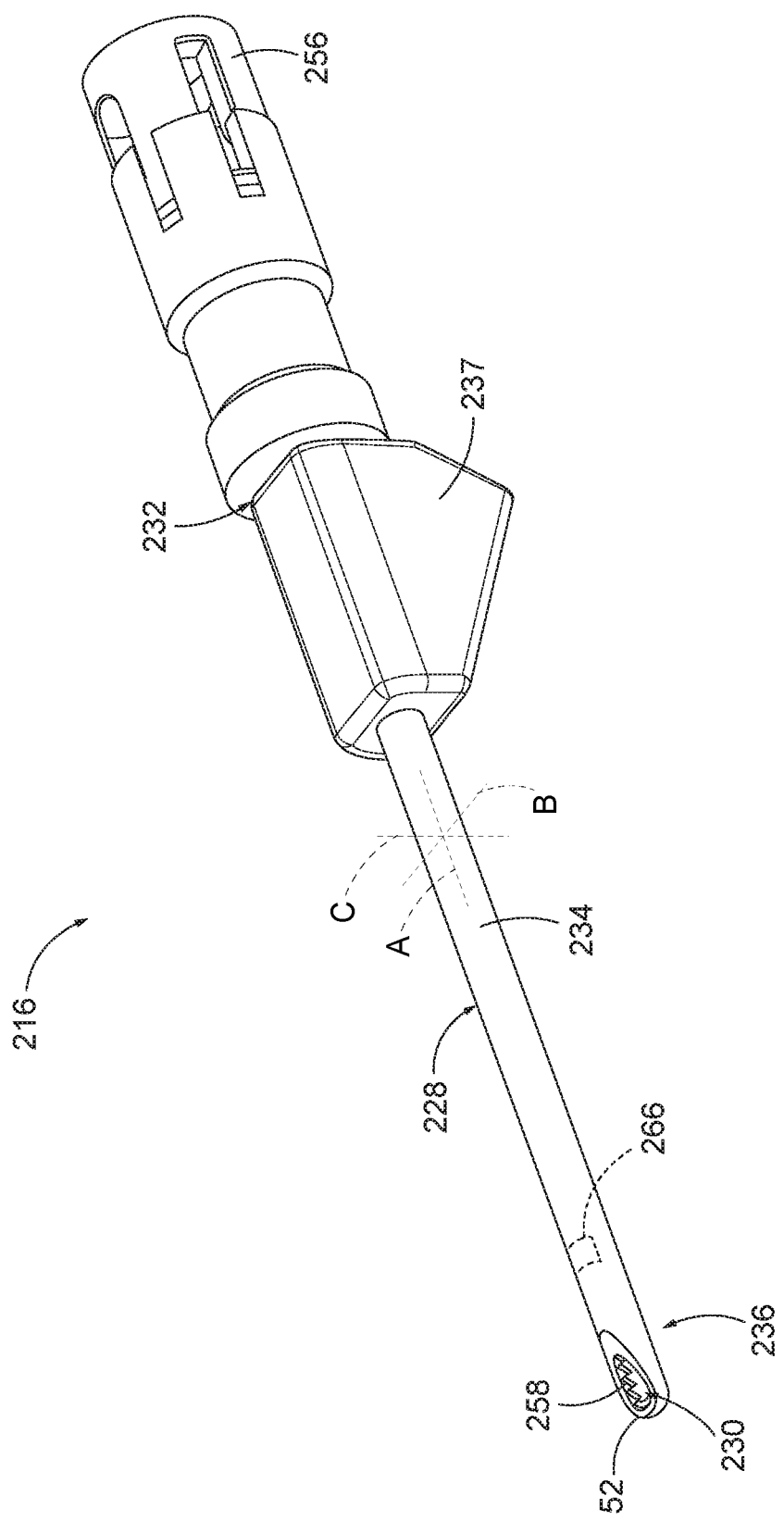
FIG. 7 depicts a perspective view of a second shaft assembly with an integrated navigation sensor.
Figure 8:
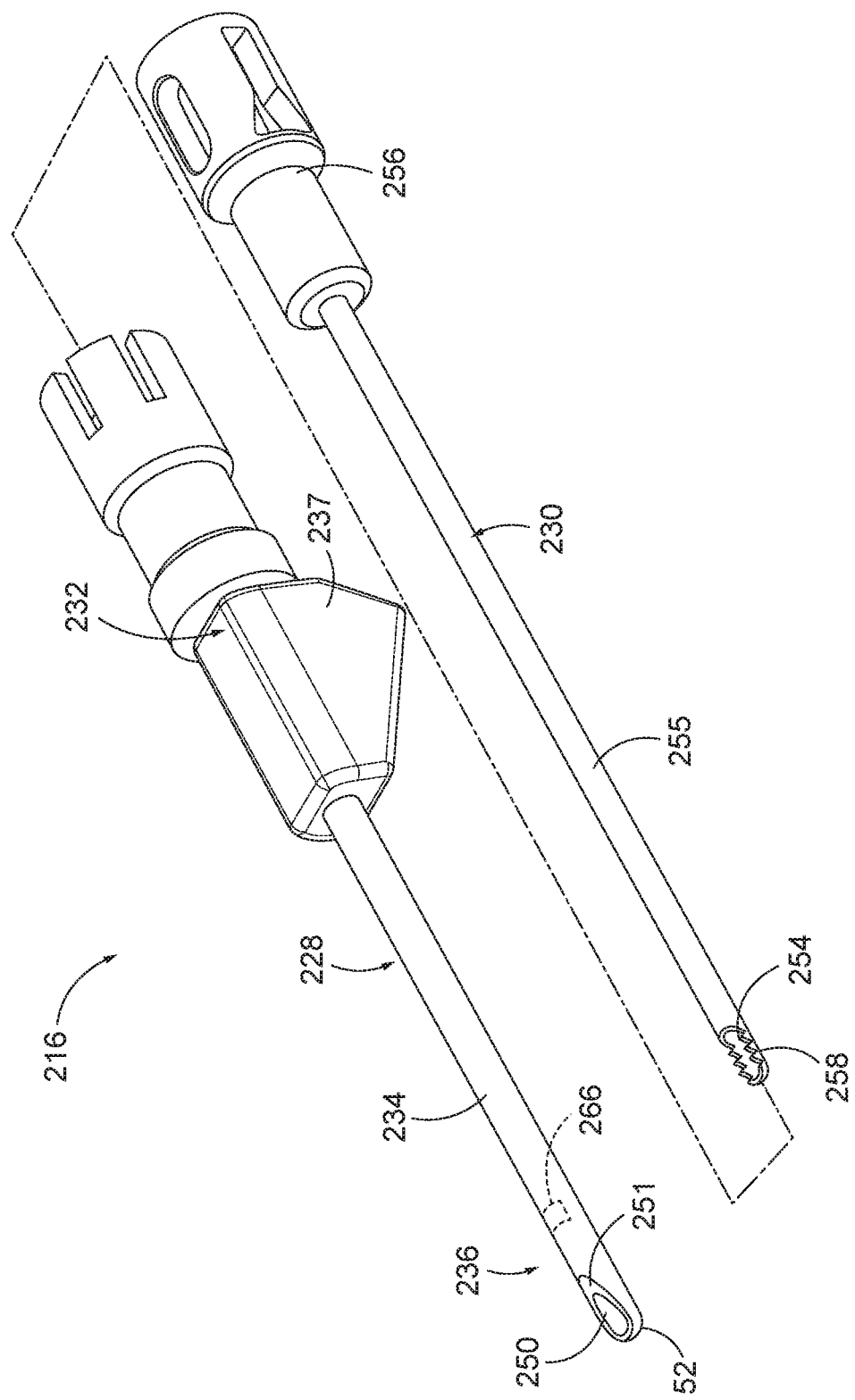
FIG. 8 depicts an exploded perspective view of the shaft assembly of FIG. 7.

FIGS. 7-8 show a second shaft assembly (216) having an integrated navigation sensor (266) for use with one or more portions of surgical cutting instrument (10) (see FIG. 1) and IGS navigation system (100) (see FIG. 3). Shaft assembly (216) includes an outer shaft (228) that removably receives an inner cutting member (230). In the present example, shaft (228) is reusable, whereas cutting member (230) is discarded and disposed of following treatment of the patient. Shaft (228) has a proximal shaft hub (232) and a tubular shaft body (234) extending distally therefrom to distal end (52). Integrated navigation sensor (266) is constructed integrally within a distal end portion (236) of a sidewall (251) of shaft body (234) and positioned proximal from a shaft window opening (250). Integrated navigation sensor (266) operatively connects with navigation system, such as IGS navigation system (100) (see FIG. 3), such that the positional movement of integrated navigation sensor (266) is calculated and tracked on a display, such as display screen (112) (see FIG. 3). In the present example, the positional movement of integrated navigation sensor (266) is correlated to the positional movement of distal end (52) based on a predetermined position of distal end (52) relative to integrated navigation sensor (266).

Proximal shaft hub (232) more particularly mechanically connects to handle assembly (12) (see FIG. 1) and electrically connects handle assembly to a remainder of an alternative navigation system (not shown) by a communications connector (237) on proximal shaft hub (232) in operative connection with integrated navigation sensor (266). Communications connector (237) is configured to receive wiring (not shown) that connects to the remainder of alternative navigation system (not shown) and communicates signal data from integrated navigation sensor (266) for calculating and tracking the positional movement of integrated navigation sensor (266). Distally positioned relative to integrated navigation sensor (266), shaft window opening (250) is longitudinally oblong and extends through a portion of sidewall (251) and through distal end (52). Shaft window opening (250) is thereby configured to receive tissue therethrough for resection by cutting member (230). In the present example, shaft body (234) is stainless steel, although alternative materials capable of insertion and manipulation within the patient may be similarly used.

Cutting member (230) has a cutting window opening (254) extending through a cutting body (255) as well as a proximal cutting hub (256) configured to mechanically connect to handle assembly (12) (see FIG. 1) for being rotatably driven. Cutting body (255) extends distally from proximal cutting hub (256) toward cutting window opening (254), which is longitudinally oblong similarly sized to align and cooperate with shaft window opening (250) to receive tissue for resection. To this end, cutting window opening (254) has a surrounding serrated cutting edge (258) configured to cut through tissue as discussed above in greater detail.

Integrated navigation sensor (266) is generally configured to be tracked by navigation system (100) to determine the positional movement of integrated navigation sensor (266), which is then correlated to the positional movement of distal end (52) within the patient during use. More particularly, integrated navigation sensor (266) may be specifically configured to respectively track the positional movement in a longitudinal direction, a lateral direction, and/or a transverse direction. As used herein, the longitudinal direction is a distal or proximal direction along a longitudinal axis (A) as shown in FIG. 7, the lateral direction is perpendicularly left to right of longitudinal axis as shown in FIG. 7 along a lateral axis (B), and the transverse direction is perpendicularly upward and downward relative to the longitudinal axis as shown in FIG. 7 along a transverse axis (C). These directional references are further applicable to the remaining examples shown in FIGS. 9-24 for clarity, but are not intended to unnecessarily limit the invention described herein.

In some versions, navigation sensor (266) comprises one or more coils of conductive wire wrapped about respective axes. Such coils are configured to generate electrical signals in response to movement within the electromagnetic field generated by field generators (102), and navigation system (100) is configured to interpret such signals to determine the position of navigation sensor (266) in three-dimensional space. In some other versions, navigation sensor (266) comprises a one or more conductive annular members centered about respective axes. Other suitable structures and configurations that may be used to form navigation sensor (266) will be apparent to those of ordinary skill in the art in view of the teachings herein.

B. Multi-Axis Navigation Sensor Arrangement with a Plurality of Navigation Sensors FIGS. 9-14 show a third shaft assembly (316) having a multi-axis navigation sensor arrangement (365) for use with one or more portions of surgical cutting instrument (10) (see FIG. 1) and IGS navigation system (100) (see FIG. 3). Multi-axis navigation sensor arrangement (365) includes an axial navigation sensor (366a), a lateral navigation sensor (366b), and a transverse navigation sensor (366c) configured to respectively sense positional movement in longitudinal, lateral, and transverse directions along shaft assembly (316). Shaft assembly (316) has an outer shaft (328) with a tubular shaft body (334) that removably receives an inner cutting member (330). Each of the axial, lateral, and transverse navigation sensors (366a, 366b, 366c) is embedded within a distal end portion (336) of a sidewall (351) of shaft body (334) and positioned proximal from a shaft window opening (350). Axial, lateral, and transverse navigation sensors (366a, 366b, 366c) operatively connect with navigation system, such as IGS navigation system (100) (see FIG. 3), such that the positional movement of axial, lateral, and transverse navigation sensors (366a, 366b, 366c) are calculated and tracked on a display, such as display screen (112) (see FIG. 3). In the present example, the positional movement of axial, lateral, and transverse navigation sensors (366a, 366b, 366c) are correlated to the positional movement of distal end (52) based on a predetermined position of distal end (52) relative to axial, lateral, and transverse navigation sensors (366a, 366b, 366c).

Figure 9:
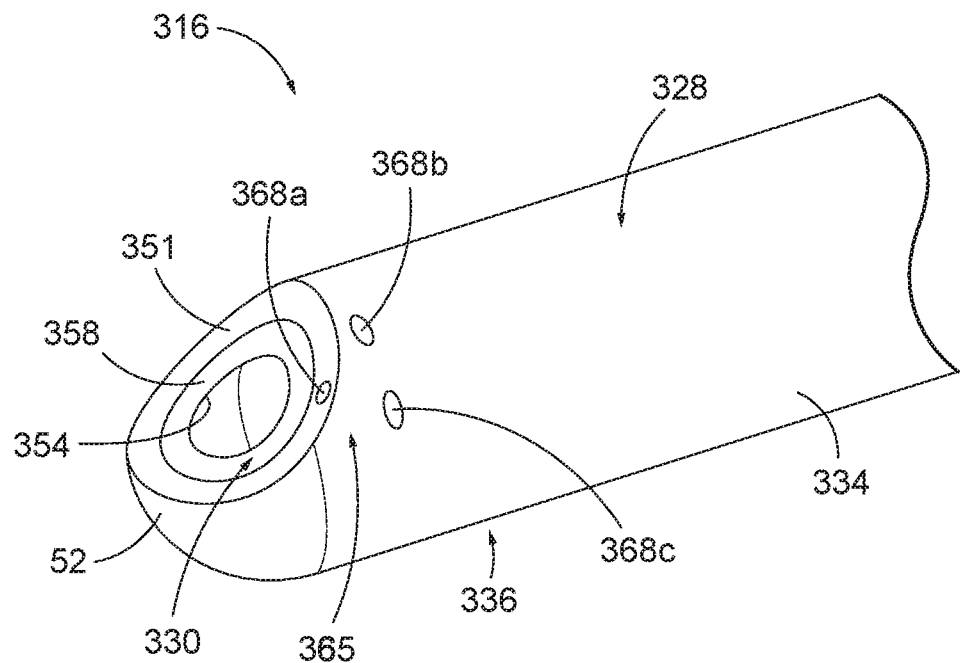
FIG. 9 depicts an enlarged perspective view of a third shaft assembly with a multi-axis navigation sensor arrangement including an axial navigation sensor, a lateral navigation sensor, and a transverse navigation sensor.
Figure 10:
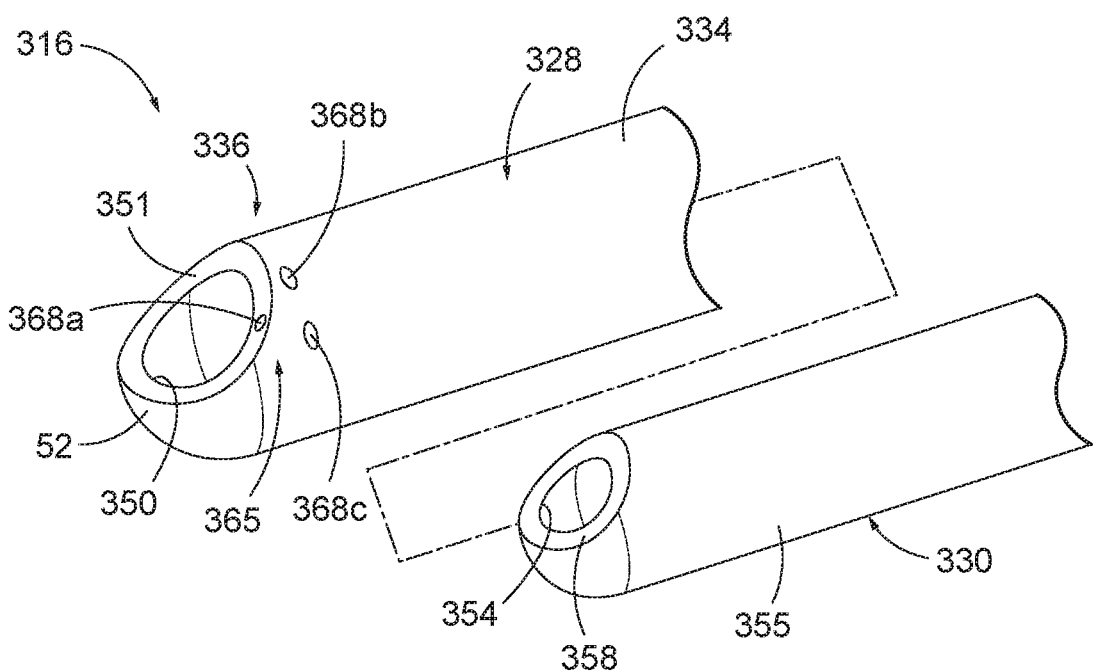
FIG. 10 depicts an exploded perspective fragmentary view of the shaft assembly of FIG. 9.
Figure 11:
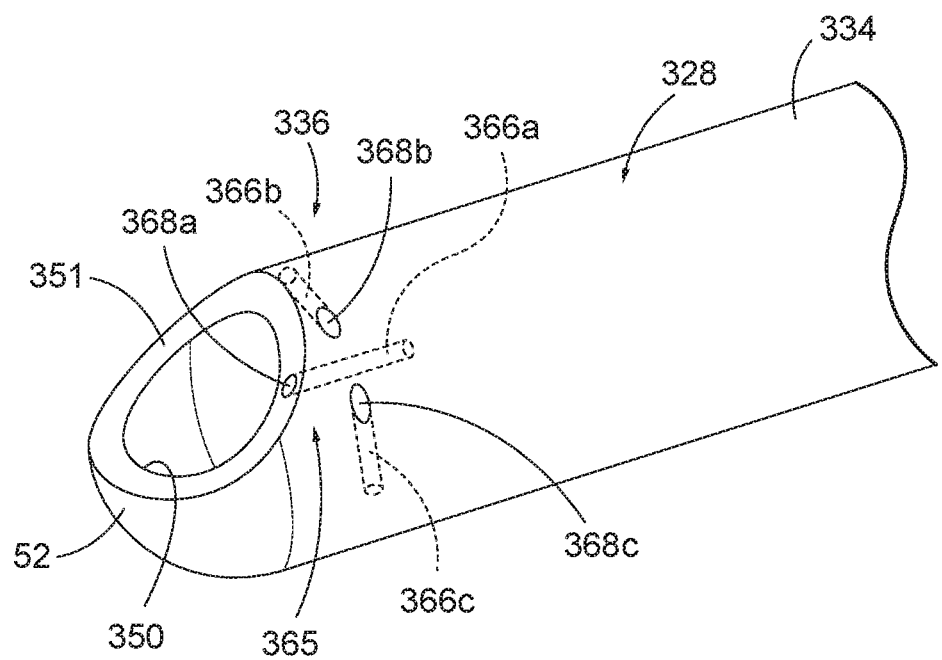
FIG. 11 depicts an enlarged perspective view of an outer shaft of the shaft assembly of FIG. 9.

With respect to FIGS. 9-10, cutting member (330) has a cutting window opening (354) extending through a cutting body (355). Cutting body (355) extends distally from a proximal cutting hub (not shown) toward cutting window opening (354), which is sized to align and cooperate with shaft window opening (350) to receive tissue for resection. To this end, cutting window opening (354) has a surrounding cutting edge (358) configured to cut through tissue as discussed above in greater detail.

Figure 12:
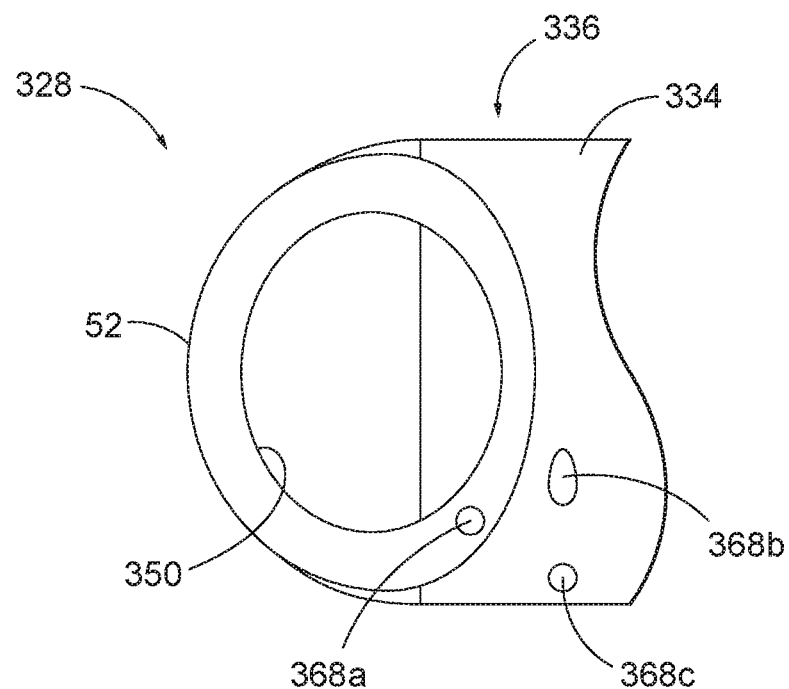
FIG. 12 depicts a front view of the outer shaft of FIG. 11.
Figure 13:
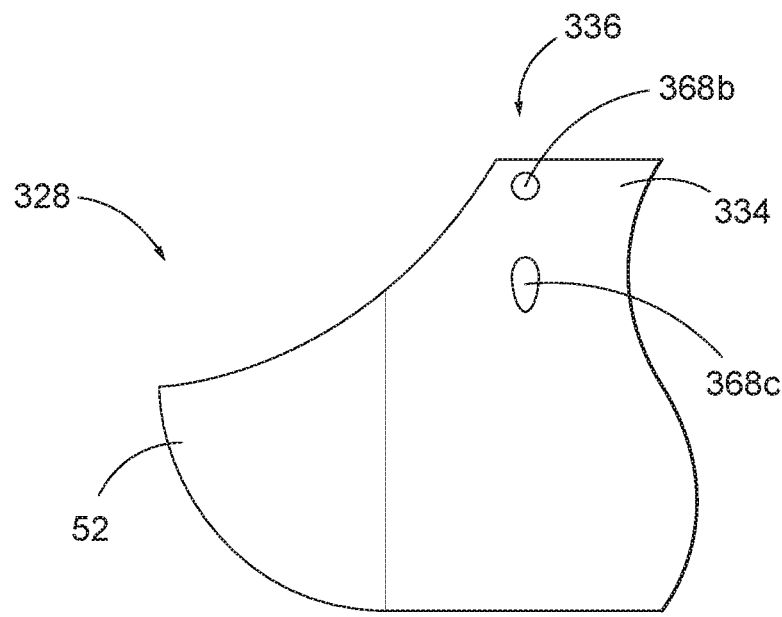
FIG. 13 depicts a side elevational view of the outer shaft of FIG. 11.
Figure 14:
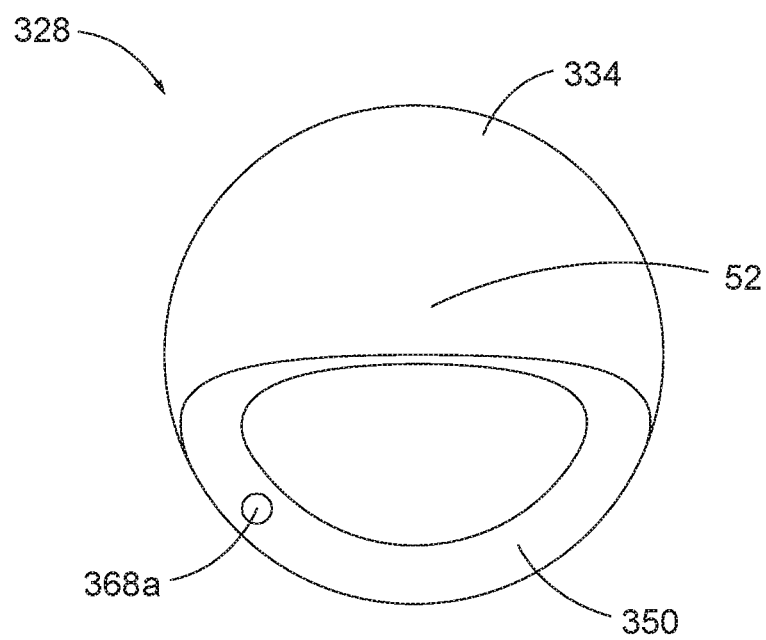
FIG. 14 depicts a distal end view of the outer shaft of FIG. 11.
Figure 15:
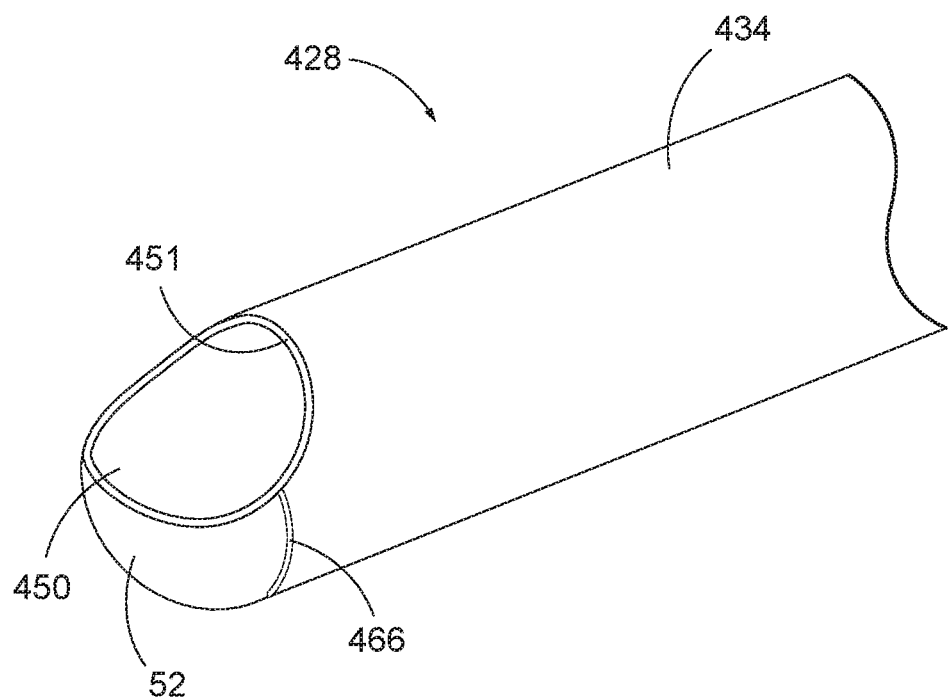
FIG. 15 depicts an alternative outer shaft of a shaft assembly with a half-wound coiled navigation sensor.

Each axial, lateral, and transverse navigation sensor (366a, 366b, 366c) is respectively positioned within an axial bore (368a), a lateral bore (368b), and a transverse bore (368c) as shown in FIGS. 11-14. Axial bore (368a) extends into sidewall (351) parallel to the longitudinal axis, lateral bore (368b) extends into sidewall (351) parallel to the lateral axis, and transverse bore (368c) extends into sidewall (351) parallel to the transverse axis. Axial bore (368a) receives axial navigation sensor (366a) to align parallel with the longitudinal axis to sense longitudinal positional movement. Lateral bore (368b) receives lateral navigation sensor (366b) to align parallel with the lateral axis to sense lateral positional movement. Transverse bore (368c) receives transverse navigation sensor (366c) to align parallel with the transverse axis to sense transverse positional movement. FIGS. 12, 13, and 14 show front, side, and distal end views that respectively align with the transverse, lateral, and longitudinal axes to view directly into transverse, lateral, and longitudinal bores (368c, 368b, 368a). Thereby, each of the longitudinal, lateral, and transverse positional movements of shaft assembly (316) (see FIG. 9) are independently tracked for component or combined viewing during use. Various suitable components and configurations that may be used to form navigation sensors (366a, 366b, 366c) will be apparent to those of ordinary skill in the art in view of the teachings herein.

C. Wound Navigation Sensor

FIGS. 15-18 show an alternative outer shaft (428) having a half-wound navigation sensor (466) for use with one or more portions of surgical cutting instrument (10) (see FIG. 1) and IGS navigation system (100) (see FIG. 3). Half-wound navigation sensor (366) bows about outer shaft (428) to sense positional movement and, more specifically, the orientation of one or more portions of outer shaft (428) within the patient. Outer shaft (428) with a tubular shaft body (434) that removably receives an inner cutting member (not shown). Half-wound navigation sensor (466) is wound about an outer surface of a sidewall (451) of shaft body (434) and positioned radially opposite from a shaft window opening (450). Half-wound navigation sensor (466) operatively connects with navigation system, such as IGS navigation system (100) (see FIG. 3), such that the positional movement of half-wound navigation sensor (466) is calculated and tracked on a display, such as display screen (112) (see FIG. 3). In the present example, the positional movement of half-wound navigation sensor (466) is correlate to the orientation, angle, and position of shaft window opening (450) based on a predetermined position of shaft window opening (450) relative to the orientation, angle, and position of half-wound navigation sensor (466) on sidewall (451).

Figure 16:
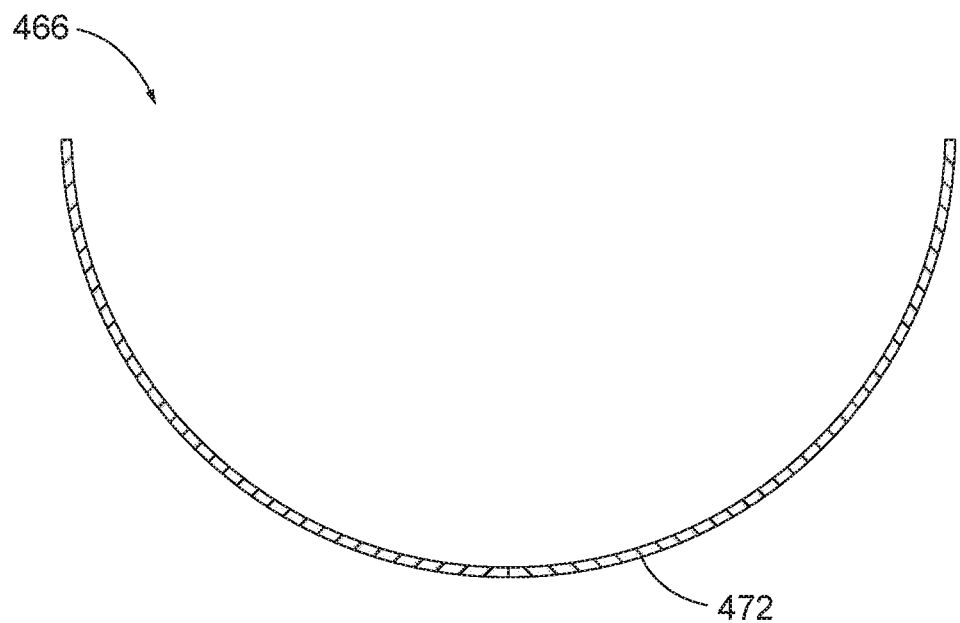
FIG. 16 depicts a distal end view of the half-wound coiled navigation sensor of FIG. 15.
Figure 17:
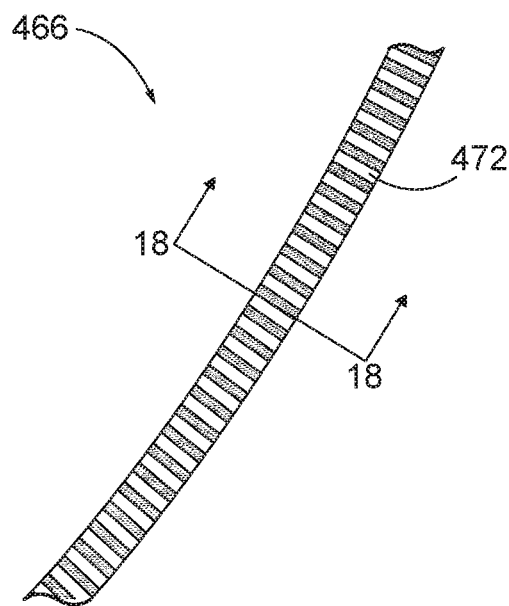
FIG. 17 depicts an enlarged distal end view of the half-wound coiled navigation sensor of FIG. 15.
Figure 18:
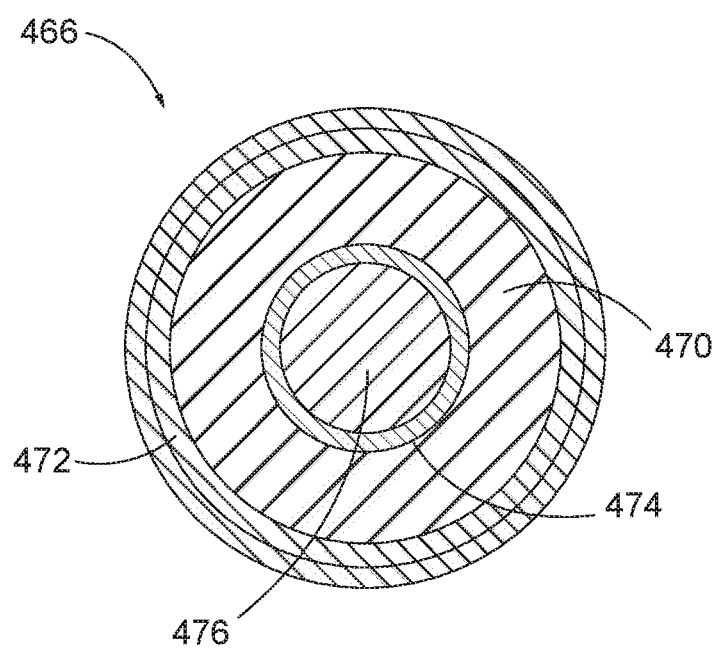
FIG. 18 depicts a cross-sectional view of the half-wound coiled navigation sensor taken along section line 18-18 of FIG. 17.
Figure 19:
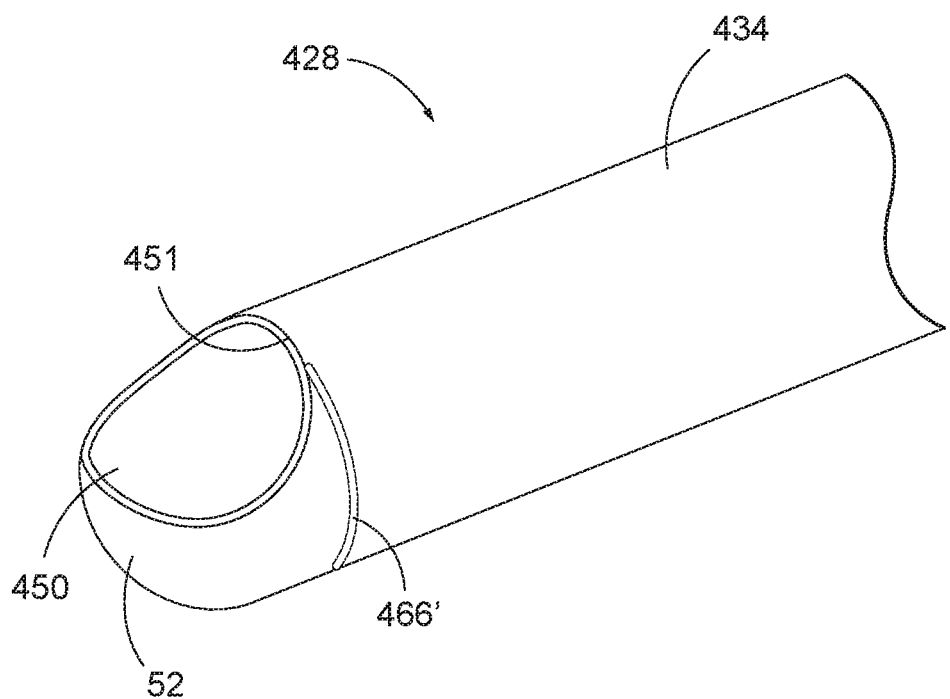
FIG. 19 depicts the outer shaft of FIG. 15 with a three-quarter-wound coiled navigation sensor.
Figure 20:
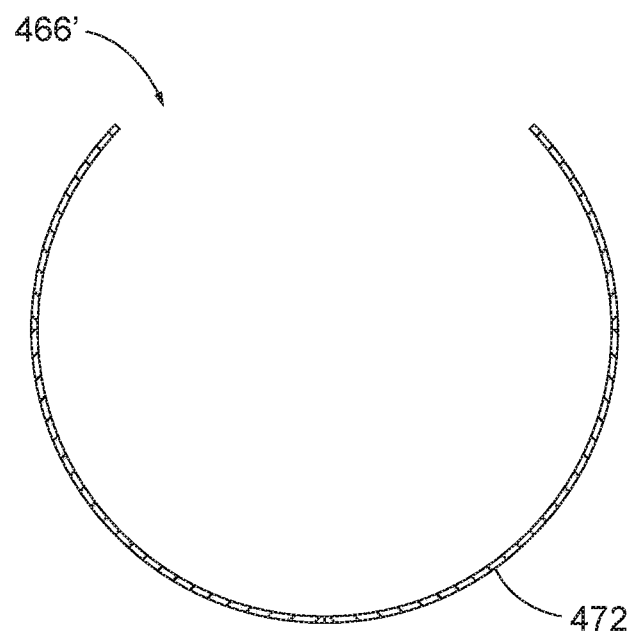
FIG. 20 depicts a distal end view of the three-quarter-wound coiled navigation sensor of FIG. 19.
Figure 21:
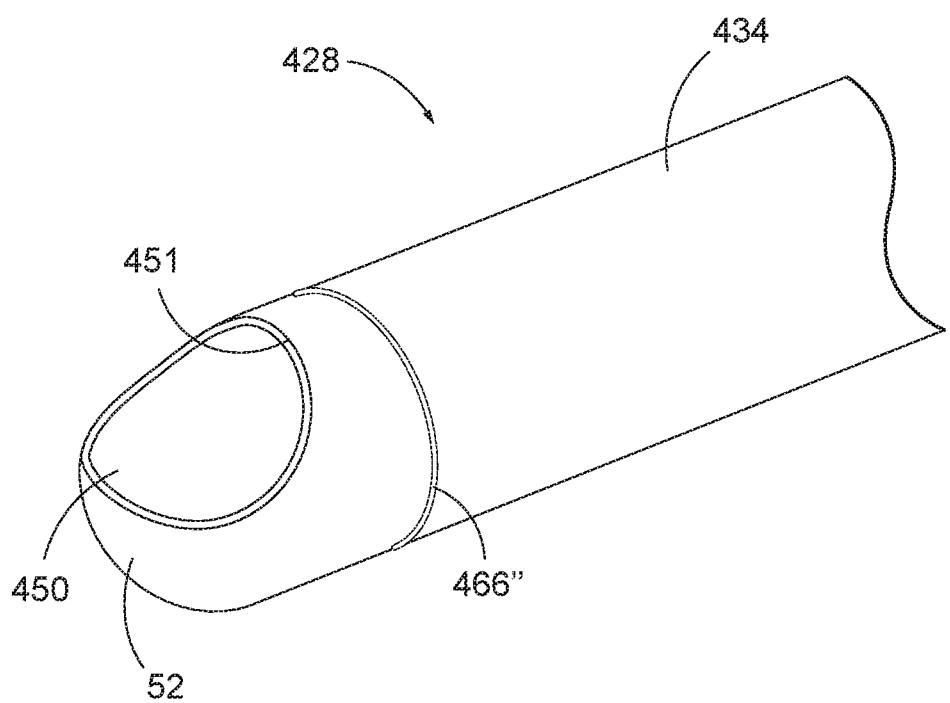
FIG. 21 depicts the outer shaft of FIG. 15 with a full-wound coiled navigation sensor.
Figure 22:
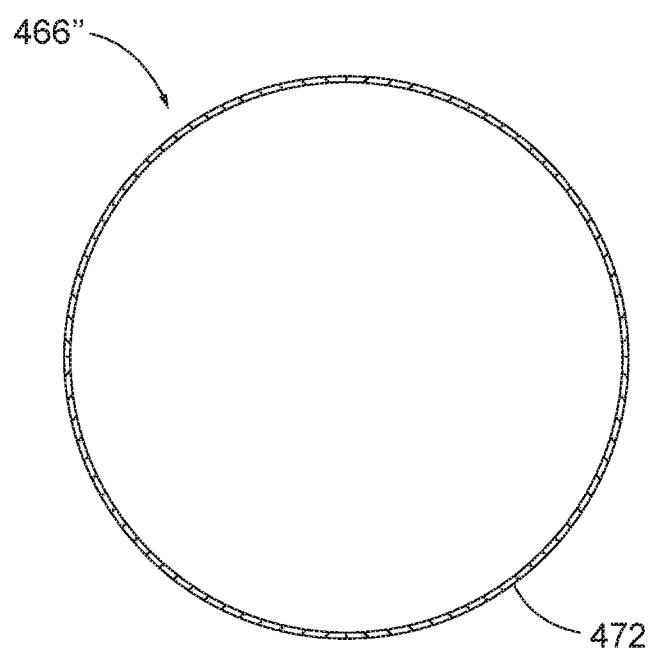
FIG. 22 depicts a distal end view of the full-wound coiled navigation sensor of FIG. 21.

With respect to FIGS. 16-18, half-wound navigation sensor (466) has a coiled body (470), such as a clockwise or counterclockwise coiling, contained between an outer tube (472) and an inner tube (474). A core material (476) is contained within the inner tube (474). In the present example, outer and inner tubes (472, 474) are polyimide, whereas core material (476) is a ferrite powder. Each of coiled body (470), outer and inner tubes (472, 474), and core material (476) extends through an entirety of half-wound navigation sensor (466) and effectively wrap about the longitudinal axis against the outer surface of sidewall (451) in predetermined position relative to shaft window opening (450). The present example of half-wound navigation sensor (466) is positioned radially opposite from shaft window opening (450) and is thus limited in length to half of the circumference about sidewall (451) so as to inhibit interference with tissue being received through shaft window opening (450) during use.

Navigation sensor (466) may be alternatively positioned and/or wound in a predetermined position relative to shaft window opening (450) for tracking. By way of example, FIGS. 19-20 and FIGS. 21-22 respectively show a three-quarter wound navigation sensor (466') and a full-wound navigation sensor (466") positioned on outer shaft (428) in place of half-wound navigation sensor (466) as discussed above. Specifically, three-quarter wound navigation sensor (466') is longitudinally positioned about shaft (428) to align with a proximal-most portion of shaft window opening (450), but angularly opposite from shaft window opening (450). In contrast, full-wound navigation sensor (466') is longitudinally positioned about shaft (428) to be positioned proximally from shaft window opening (450) while encircling the outer surface of sidewall (451). The invention is thus not intended to be unnecessarily limited to the particularly wound navigation sensors (466, 466', 466") show and described herein.

D. Annular Navigation Sensor

Figure 23:
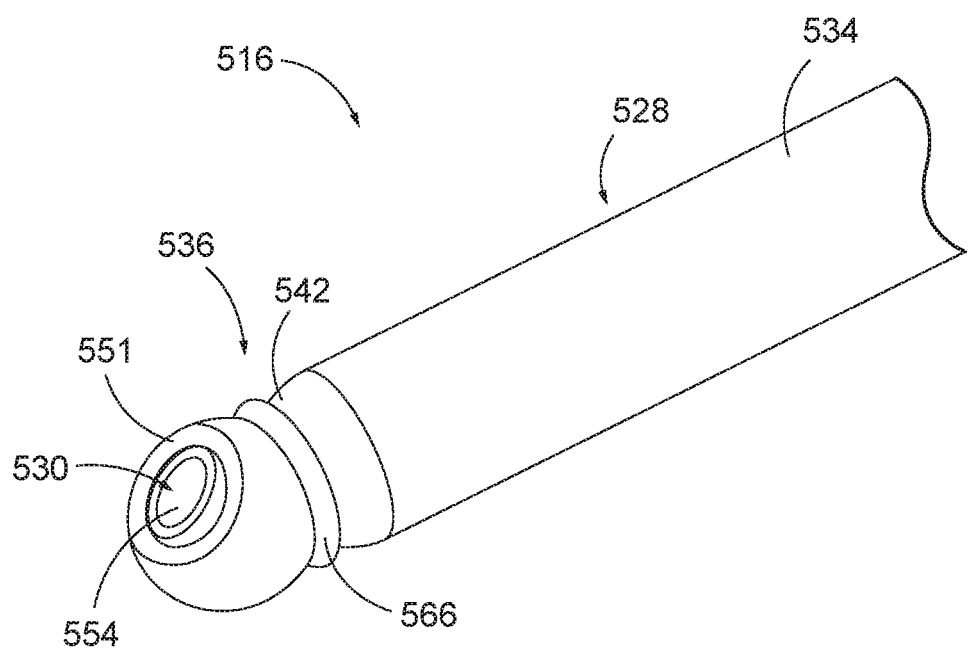
FIG. 23 depicts an enlarged perspective view of a fourth shaft assembly having a necked cutting member and a necked outer shaft with an annular navigation sensor.
Figure 24:
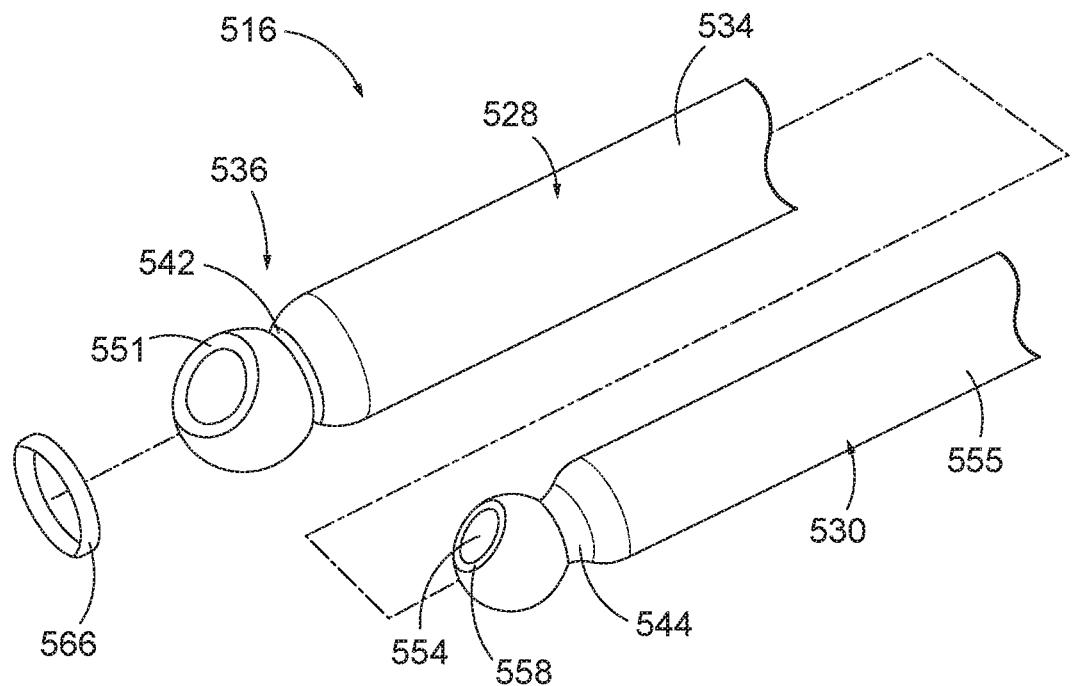
FIG. 24 depicts an exploded perspective fragmentary view of the shaft assembly of FIG. 23.

FIGS. 23-24 show a fourth shaft assembly (516) having an annular navigation sensor (566) for use with one or more portions of surgical cutting instrument (10) (see FIG. 1) and IGS navigation system (100) (see FIG. 3). Shaft assembly (516) has a necked outer shaft (528) with a hollow shaft body (534) that removably receives a necked inner cutting member (530). A distal end portion (536) of shaft body (534) tapers inward to define an annular shaft channel (542) about a sidewall (551) of shaft body (534). Similarly, a cutting body (555) of cutting member (530) tapers inward to an annular cutting channel (544), which is configured to receive the necked down portion of sidewall (551) when shaft (528) receives cutting member (530) for use. Generally, annular navigation sensor (566) is configured to be received within annular shaft channel (542) such that the necked down portion of sidewall (551) captures annular navigation sensor (566) thereon. Annular navigation sensor (566) operatively connects with navigation system, such as IGS navigation system (100) (see FIG. 3), such that the positional movement of annular navigation sensor (566) is calculated and tracked on a display, such as display screen (112) (see FIG. 3). In the present example, the positional movement of annular navigation sensor (566) is axial movement along the longitudinal axis of shaft assembly (516).

Cutting member (530) has a cutting window opening (554) extending through cutting body (555). Cutting window opening (554) is more particularly sized to align and cooperate with shaft window opening (550) to receive tissue for resection. To this end, cutting window opening (554) has a surrounding cutting edge (558) configured to cut through tissue as discussed above in greater detail. Furthermore, in the present example, a portion of cutting member (530) extending distally from annular shaft channel (542) is resiliently deflectable to allow for insertion through the necked down portion of sidewall (551) during assembly and/or disassembly. Alternative structures and methods of assembly to insert cutting member (530) operatively into shaft (528), and the invention is not intended to be unnecessarily limited to cutting member (530) with resiliently deflectable portions.

Outer shaft (528) defines an outer radial profile larger than annular shaft channel (542), which otherwise fits within the outer radial profile. Annular shaft channel (542) and annular navigation sensor (566) are each respectively sized in the radial direction such that even with annular navigation sensor (566) positioned within annular shaft channel (542), annular navigation sensor (566) remains within the outer radial profile. In other words, annular navigation sensor (566) does not extend radially outward beyond the outer radial profile of outer shaft (528) to reduce the likelihood of annular navigation sensor (566) catching on the anatomy or other structure during use. Annular navigation sensor (566) in various example may radially extend outward to align with outer radial profile and still be considered to remain within the outer radial profile as described herein. By way of further example, a cover (not shown) may be positioned about shaft assembly (516) and proximally extend from the necked down portion of sidewall (551) over annular navigation sensor (566) to further inhibit annular navigation sensor (566) from catching on the anatomy or other structure.

Annular navigation sensor (566) is configured to be tracked by navigation system (100) to determine the axial movement of annular navigation sensor (266), which is then correlated to the axial movement of one or more portions of shaft assembly (516) within the patient during use. Annular navigation sensor (566) may be additionally or alternatively configured to determine one or more other aspects of positional movement, such as lateral movement, transverse movement, or orientation. The present invention is thus not intended to be unnecessarily limited to sensing axial movement. Various suitable components and configurations that may be used to form navigation sensor (566) will be apparent to those of ordinary skill in the art in view of the teachings herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a shaft extending along a longitudinal axis and including: (i) a shaft lumen extending along the longitudinal axis, (ii) a shaft window opening in fluid communication with an environment and the shaft lumen and configured to receive tissue therein from the environment, and (iii) a shaft edge at least partially surrounding the shaft window opening; (b) a cutting member disposed within the shaft lumen and configured to cyclically move from a first position to a second position relative to the shaft, wherein the cutting member includes: (i) a cutting window opening in fluid communication with the shaft window opening in the first position and configured to receive the tissue therein, (ii) a cutting edge at least partially surrounding the cutting window opening and configured to be cyclically moved within the shaft lumen adjacent to the shaft edge for cutting a tissue portion from the tissue between the cutting edge and the shaft edge, and (iii) a suction lumen extending along the longitudinal axis in fluid communication with the cutting window opening and configured to connect to a vacuum source, wherein the suction lumen is in fluid communication with the cutting window opening and the shaft window opening in the first position; and (c) a navigation system including a first navigation sensor, wherein the first navigation sensor is positioned on at least one of the shaft or the cutting member and configured to be tracked within a patient for identifying a positional movement of the shaft or the cutting member within the patient.

Example 2

The surgical instrument of Example 1, wherein the first navigation sensor is positioned on the shaft, and wherein the first navigation sensor is configured to be tracked for identifying the positional movement of the shaft while cutting the tissue portion from the tissue.

Example 3

The surgical instrument of Example 2, wherein the shaft includes a distal shaft end portion, and wherein the first navigation sensor is integrated into the distal shaft end portion.

Example 4

The surgical instrument of any one or more of Examples 2 through 3, wherein the first navigation sensor is positioned on the cutting member about the longitudinal axis, and wherein the first navigation sensor is configured to sense an orientation of the shaft window opening.

Example 5

The surgical instrument of Example 4, wherein the first navigation sensor is positioned on an outer surface of the cutting member and at least partially surrounds the longitudinal axis.

Example 6

The surgical instrument of Example 5, wherein the first navigation sensor comprises a sensor coil.

Example 7

The surgical instrument of any one or more of Examples 5 through 6, wherein the first navigation sensor is positioned radially opposite from the shaft window opening.

Example 8

The surgical instrument of any one or more of Examples 1 through 7, wherein the first navigation sensor is configured to sense at least one of an axial movement parallel to the longitudinal axis, a lateral movement perpendicular to the longitudinal axis along a lateral axis, or a transverse movement perpendicular to each of the longitudinal and lateral axes along a transverse axis.

Example 9

The surgical instrument of Example 8, wherein the navigation system further includes a first sensor bore extending along at least one of the longitudinal, lateral, or transverse axes through at least one of the shaft or the cutting member, and wherein the first navigation sensor is received within the first sensor bore.

Example 10

The surgical instrument of Example 9, wherein the first sensor bore extends through the shaft and receives the first navigation sensor therein to position the first navigation sensor in the shaft.

Example 11

The surgical instrument of any one or more of Examples 9 through 10, wherein the navigation system further includes a second navigation sensor and a second sensor bore, wherein the second sensor bore extends along at least one of the remaining longitudinal, lateral, or transverse axes through at least one of the shaft or the cutting member, and wherein the second navigation sensor is received within the second sensor bore.

Example 12

The surgical instrument of Example 11, wherein the navigation system further includes a third navigation sensor and a third sensor bore, wherein the first sensor bore extends along the longitudinal axis and receives the first navigation sensor therein such that the first navigation sensor is configured to sense longitudinal movement, wherein the second sensor bore extends along the lateral axis and receives the second navigation sensor therein such that the second navigation sensor is configured to sense lateral movement, and wherein the third sensor bore extends along the transverse axis and receives the third navigation sensor therein such that the third navigation sensor is configured to sense transverse movement.

Example 13

The surgical instrument of Example 12, wherein the first sensor bore extends through the shaft and receives the first navigation sensor therein to position the first navigation sensor in the shaft, wherein the second sensor bore extends through the shaft and receives the second navigation sensor therein to position the second navigation sensor in the shaft, and wherein the third sensor bore extends through the shaft and receives the third navigation sensor therein to position the third navigation sensor in the shaft.

Example 14

The surgical instrument of any one or more of Examples 8 through 13, wherein the shaft defines an outer radial profile about the longitudinal axis and includes an annular channel about the shaft that extends radially inward of the outer radial profile, wherein the first navigation sensor is configured to be received within the annular channel such that the first navigation sensor remains within the outer radial profile about the longitudinal axis.

Example 15

The surgical instrument of any one or more of Examples 1 through 14, wherein the first navigation sensor is configured to generate a positional movement signal data and the navigation system further includes: (i) a processor operatively connected to the first navigation sensor and configured to receive the positional movement signal and process the positional movement signal to track the positional movement of the first navigation sensor, and (ii) a display screen operatively connected to the processor, wherein the display screen is configured to visually indicate the tracked positional movement of the first navigation sensor.

Example 16

A surgical instrument, comprising: (a) a handle assembly including: (i) a body, (ii) a suction port configured to be connected to a vacuum source, and (iii) a motorized drive assembly; and (b) a shaft assembly extending distally from the handle assembly and including: (i) a shaft extending along a longitudinal axis having: (A) a shaft lumen extending along the longitudinal axis, (B) a shaft window opening in fluid communication with an environment and the shaft lumen and configured to receive a tissue therein from the environment, and (C) a shaft edge at least partially surrounding the shaft window opening, (ii) a cutting member disposed within the shaft lumen and connected to the motorized drive assembly, wherein the motorized drive assembly is configured to cyclically move the cutting member from a first position to a second position relative to the shaft, wherein the cutting member includes: (A) a cutting window opening in fluid communication with the shaft window opening in the first position and configured to receive the tissue therein, (B) a cutting edge at least partially surrounding the cutting window opening and configured to be cyclically moved within the shaft lumen adjacent to the shaft edge for cutting a tissue portion from the tissue between the cutting edge and the shaft edge, and (C) a suction lumen extending along the longitudinal axis in fluid communication with the cutting window opening and fluidly connected to the suction port, wherein the suction lumen is in fluid communication with the cutting window opening and the shaft window opening in the first position, and (c) a navigation system including a navigation sensor, wherein the navigation sensor is positioned on at least one of the shaft or the cutting member and configured to be tracked within a patient for identifying a positional movement of the shaft or the cutting member within the patient.

Example 17

The surgical instrument of Example 16, wherein the cutting member is configured to be removed from within the shaft for reuse of the shaft and disposal of the cutting member.

Example 18

The surgical instrument of any one or more of Examples 16 through 17, wherein the navigation sensor is configured to generate a positional movement signal data and the navigation system further includes: (i) a processor operatively connected to the navigation sensor and configured to receive the positional movement signal and process the positional movement signal to track the positional movement of the navigation sensor, and (ii) a display screen operatively connected to the processor, wherein the display screen is configured to visually indicate the tracked positional movement of the navigation sensor.

Example 19

A method of tracking a positional movement of a surgical instrument, wherein the surgical instrument has a shaft, a cutting member, and navigation sensor positioned on at least one of the shaft or the cutting member, wherein the shaft extends along a longitudinal axis and includes a shaft window opening in fluid communication with an environment, wherein the cutting member is disposed within the shaft and is configured to cyclically move from a first position to a second position relative to the shaft, wherein the cutting member includes a cutting edge and a suction lumen extending along the longitudinal axis, wherein the suction lumen is operatively connected to a vacuum source, and wherein the aspiration vent extends through at least one of the shaft or the cutting member, the method comprising: (a) inserting the shaft and the cutting member into a passageway about an anatomy within a patient; (b) communicating a positional movement signal data from the navigation sensor within the passageway to a processor; and (c) tracking the positional movement of the cutting member and the shaft within the passageway.

Example 20

The method of Example 19, further comprising: (a) cutting a tissue portion from a mass of tissue with the cutting edge of the cutting member in a first position; (b) cyclically moving the cutting member relative to the shaft from the first position to the second position; and (c) suctioning an airflow from the environment through the suction lumen.

V. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
    (a) a shaft extending along a longitudinal axis and including:
        (i) a shaft lumen extending along the longitudinal axis,
        (ii) a shaft window opening in fluid communication with an environment and the shaft lumen and configured to receive tissue therein from the environment, and (iii) a shaft edge at least partially surrounding the shaft window opening;
(b) a cutting member disposed within the shaft lumen and configured to cyclically move from a first position to a second position relative to the shaft, wherein the cutting member includes:
  (i) a cutting window opening in fluid communication with the shaft window opening in the first position and configured to receive the tissue therein,
  (ii) a cutting edge at least partially surrounding the cutting window opening and configured to be cyclically moved within the shaft lumen adjacent to the shaft edge for cutting a tissue portion from the tissue between the cutting edge and the shaft edge, and
  (iii) a suction lumen extending along the longitudinal axis in fluid communication with the cutting window opening and configured to connect to a vacuum source, wherein the suction lumen is in fluid communication with the cutting window opening and the shaft window opening in the first position; and
(c) a navigation system including:
  (i) a first navigation sensor, wherein the first navigation sensor is positioned on at least one of the shaft or the cutting member and configured to be tracked within a patient for identifying a positional movement of the shaft or the cutting member within the patient, wherein the first navigation sensor is configured to sense an axial movement parallel to the longitudinal axis,
  (ii) a first sensor bore extending along a second axis parallel to the longitudinal axis through an exterior surface of the shaft or the cutting member, and wherein the first navigation sensor is received within the first sensor bore,
  (iii) a second navigation sensor, and
  (iv) a second sensor bore, wherein the second sensor bore extends along at least one of a lateral axis or a transverse axis through at least one of the shaft or the cutting member, wherein the second navigation sensor is received within the second sensor bore.

2. The surgical instrument of claim 1, wherein the exterior surface is defined by the shaft at a position adjacent to the shaft window opening, and wherein the first navigation sensor is configured to be tracked for identifying the positional movement of the shaft while cutting the tissue portion from the tissue.

3. The surgical instrument of claim 1, wherein the exterior surface is defined by the cutting member adjacent to the cutting window opening, and wherein the first navigation sensor is configured to sense an orientation of the shaft window opening.

4. The surgical instrument of claim 1, wherein the first sensor bore extends through the shaft and receives the first navigation sensor therein to position the first navigation sensor in the shaft.

5. The surgical instrument of claim 1, wherein the navigation system further includes a third navigation sensor and a third sensor bore, wherein the second sensor bore extends along the lateral axis and receives the second navigation sensor therein such that the second navigation sensor is configured to sense lateral movement, and wherein the third sensor bore extends along the transverse axis and receives the third navigation sensor therein such that the third navigation sensor is configured to sense transverse movement.

6. The surgical instrument of claim 5, wherein the second sensor bore extends through the shaft and receives the second navigation sensor therein to position the second navigation sensor in the shaft, and wherein the third sensor bore extends through the shaft and receives the third navigation sensor therein to position the third navigation sensor in the shaft.

7. The surgical instrument of claim 1, wherein the first navigation sensor is configured to generate a positional movement signal data and the navigation system further includes:
  (i) a processor operatively connected to the first navigation sensor and configured to receive the positional movement signal data and process the positional movement signal data to track the positional movement of the first navigation sensor, and
  (ii) a display screen operatively connected to the processor, wherein the display screen is configured to visually indicate the tracked positional movement of the first navigation sensor.

8. The surgical instrument of claim 1, wherein the cutting member is configured to be removed from within the shaft for reuse of the shaft and disposal of the cutting member.

9. A surgical instrument, comprising:
(a) a handle assembly including:
  (i) a body,
  (ii) a suction port configured to be connected to a vacuum source, and
  (iii) a motorized drive assembly; and
(b) a shaft assembly extending distally from the handle assembly and including:
  (i) a shaft extending along a longitudinal axis, wherein the shaft includes a distal portion having:
    (A) a shaft lumen extending along the longitudinal axis,
    (B) a shaft window opening in fluid communication with an environment and the shaft lumen and configured to receive a tissue therein from the environment, and
    (C) a shaft edge at least partially surrounding the shaft window opening, and
  (ii) a cutting member disposed within the shaft lumen and connected to the motorized drive assembly, wherein the motorized drive assembly is configured to cyclically move the cutting member from a first position to a second position relative to the shaft, wherein the cutting member includes:
    (A) a cutting window opening in fluid communication with the shaft window opening in the first position and configured to receive the tissue therein,
    (B) a cutting edge at least partially surrounding the cutting window opening and configured to be cyclically moved within the shaft lumen adjacent to the shaft edge for cutting a tissue portion from the tissue between the cutting edge and the shaft edge, and
    (C) a suction lumen extending along the longitudinal axis in fluid communication with the cutting window opening and fluidly connected to the suction port, wherein the suction lumen is in fluid communication with the cutting window opening and the shaft window opening in the first position; and
(c) a navigation system including a navigation sensor, wherein the navigation sensor is positioned on the shaft and configured to be tracked within a patient for identifying a positional movement of the shaft within the patient, wherein the navigation sensor is configured to wrap at least partially circumferentially around an exterior of the distal portion of the shaft about the longitudinal axis, wherein the navigation sensor is positioned radially opposite from the shaft window opening.

10. The surgical instrument of claim 9, wherein the cutting member is configured to be removed from within the shaft for reuse of the shaft and disposal of the cutting member.

11. The surgical instrument of claim 9, wherein the navigation sensor is configured to generate a positional movement signal data and the navigation system further includes:
 (i) a processor operatively connected to the navigation sensor and configured to receive the positional movement signal data and process the positional movement signal data to track the positional movement of the navigation sensor, and
 (ii) a display screen operatively connected to the processor, wherein the display screen is configured to visually indicate the tracked positional movement of the navigation sensor.

12. The surgical instrument of claim 9, wherein the navigation sensor is configured to wrap fully circumferentially around the distal portion of the shaft about the longitudinal axis.

13. The surgical instrument of claim 9, wherein the navigation sensor comprises a sensor coil.

14. A surgical instrument, comprising:
 (a) a shaft extending along a longitudinal axis and including:
  (i) a shaft lumen extending along the longitudinal axis,
  (ii) a shaft window opening in fluid communication with an environment and the shaft lumen and configured to receive tissue therein from the environment, and
  (iii) a shaft edge at least partially surrounding the shaft window opening;
 (b) a cutting member disposed within the shaft lumen and configured to cyclically move from a first position to a second position relative to the shaft, wherein the cutting member includes:
  (i) a cutting window opening in fluid communication with the shaft window opening in the first position and configured to receive the tissue therein, and
  (ii) a cutting edge at least partially surrounding the cutting window opening and configured to be cyclically moved within the shaft lumen adjacent to the shaft edge for cutting a tissue portion from the tissue between the cutting edge and the shaft edge,
 (c) a navigation system including:
  (i) a first navigation sensor configured to be tracked within a patient for identifying a positional movement of the shaft within the patient, wherein the first navigation sensor is configured to sense an axial movement parallel to the longitudinal axis,
  (ii) a second navigation sensor configured to be tracked within a patient for identifying a positional movement of the shaft within the patient, wherein the second navigation sensor is configured to sense one of a lateral or transverse axes movement of the shaft relative to the longitudinal axis,
  (iii) a first sensor bore extending through a portion of the shaft adjacent to the shaft window opening, wherein the first navigation sensor is received within the first sensor bore, wherein the first sensor bore extends parallel to the longitudinal axis such that the first navigation sensor is configured to sense longitudinal movement,
  (iv) a second sensor bore through the portion of the shaft adjacent to the shaft window opening, wherein the second navigation sensor is received within the second sensor bore, wherein the second sensor bore extends lateral to the longitudinal axis and receives the second navigation sensor therein such that the second navigation sensor is configured to sense lateral movement,
  (v) a third navigation sensor configured to be tracked within a patient for identifying a positional movement of the shaft within the patient, and
  (vi) a third sensor bore extending through the shaft, wherein the third navigation sensor is received within the third sensor bore.

15. The surgical instrument of claim 14, further comprising a suction lumen extending along the longitudinal axis in fluid communication with the cutting window opening, wherein the suction lumen is in fluid communication with the cutting window opening and the shaft window opening in the first position.

16. The surgical instrument of claim 14, wherein the cutting member is configured to be removed from within the shaft for reuse of the shaft and disposal of the cutting member.

* * * * *